United States Patent [19] [11] 4,359,724
Zimmerman et al. [45] Nov. 16, 1982

[54] EYELID MOVEMENT DETECTOR

[75] Inventors: Ronald R. Zimmerman, 302 Foxboro, Saginaw, Mich. 48602; W. Scott Bartky, Chicago, Ill.

[73] Assignee: Ronald R. Zimmerman, Flint, Mich.

[21] Appl. No.: 144,405

[22] Filed: Apr. 28, 1980

[51] Int. Cl.[3] .......................... G08B 21/00; A61B 5/04

[52] U.S. Cl. ..................................... 340/575; 128/644; 128/733; 340/576

[58] Field of Search ................ 340/575, 576; 128/733, 128/782, 644

[56] References Cited

U.S. PATENT DOCUMENTS

| | | | |
|---|---|---|---|
| 2,902,030 | 9/1959 | Kennedy et al. | 128/733 |
| 3,889,251 | 6/1975 | Litman | 340/575 |
| 3,998,213 | 12/1976 | Price | 128/644 |
| 4,144,531 | 3/1979 | Anbergen | 340/575 |
| 4,155,352 | 5/1979 | Toglia et al. | 128/733 |

FOREIGN PATENT DOCUMENTS

| | | | |
|---|---|---|---|
| 2901865 | 7/1979 | Fed. Rep. of Germany | 340/575 |

*Primary Examiner*—Glen R. Swann, III
*Attorney, Agent, or Firm*—Dressler, Goldsmith, Shore, Sutker & Milnamow, Ltd.

[57] ABSTRACT

An eyelid movement detector, includes one electrode to be placed above each eyebrow of an individual and a third electrode to serve as a ground or reference. The electrodes sense eyelid muscle activity and produce a voltage in response to eyelid movement, indicative of a state of awareness. The sensed voltage produced is amplified and compared to a threshold reference voltage by a comparator, which produces a control signal if the sensed voltage is greater than the threshold voltage. The control signal resets a timer. If the timer is not reset within a predetermined time interval, an alarm is activated to warn an individual.

18 Claims, 4 Drawing Figures

EYELID MOVEMENT DETECTOR

BACKGROUND OF THE INVENTION

1. Field of the Invention

This invention relates to alertness detection systems and more particularly to a system to detect alertness or consciousness activity by eyelid movement.

2. Description of the Prior Art

Various mechanical and electrical devices have been tried in order to warn an individual that he is becoming drowsy, but none has been shown to be of practical or commercial value. If viable, such devices would be useful for drivers to prevent loss of alertness and sleeping at the wheel, a cause of many accidents.

For instance, one electronic safety alarm consists of a lightweight plastic device which coils around the person's ear and sounds a buzzer when his head nods. The disadvantages of such a device are that mental alertness is lost long before an individual's head nods, and the device can be falsely triggered when the individual moves his head voluntarily.

Another example of a warning device is a button steering wheel alarm which must be continually depressed in order to keep the alarm from sounding. Similar to this steering wheel button is a foot pedal which requires the individual to hold a button down with his left foot while driving or operating other machinery. However, these devices would sound the alarm falsely when the hands and feet were used to operate the automobile or other machinery. Further, they rely on the assumption that less pressure or force is applied to the controls as the degree of alertness of the operator decreases, an assumption that is subject to dispute.

Other devices have employed the detection and measurement of physiological data to detect the state of drowsiness. A device used in the laboratory, the electroencephalograph (eeg), has been an effective way of monitoring alertness in an individual. This device plots brain voltages against time but, because the wave form obtained is not necessarily a periodic function, the device is of limited usefulness. Furthermore, these voltages are of extremely low amplitude and require recording apparatus which displays excellent noise rejection characteristics. Also, this device fails in practical applications since it is not small, light, easy to adjust, simple to operate or easy to maintain. Although portable alpha wave machines are available, the range of individual differences in the amount and frequency of alpha rhythm patterns is significant and relatively independent of alertness, and in addition some normal people do not exhibit an alpha rhythm.

Attempts have been made to measure tension of the supraorbital muscles and to correlate this muscle tension directly with alertness. Bipolar electrodes were placed over the supraorbital regions of an individual to sense muscle tension. These attempts encountered technical problems for various reasons. Even the portable model was quite sizable and heavy. Furthermore there was AC line interference whenever it was removed from the laboratory, and there was a high noise level of the amplification system.

Thus, there has been a failure to provide a reliable system to detect reduction in alertness at an early stage of the drowsiness sequence. Further, the devices that have attempted to detect drowsiness have been bulky, heavy, unreliable, unable to discriminate against noise interference, not easy to maintain, and not suitable of being used by a wide range of individuals.

SUMMARY OF THE INVENTION

The instant invention monitors eyelid movement activity. It has been found that a decrease in eyelid movement activity occurs as one of the first events in a sequence which results in tiredness and drowsiness. Tests have shown that when an individual fails to blink during a period of time, e.g., a 15 second interval, drowsiness is commencing. The decrease or absence of eye blinks is associated with open-eye staring at the road or into space and a corresponding loss of alertness.

Detection of this decreased eyelid movement activity is desirable because an individual can be warned of his drowsiness and decreased alertness before an accident occurs, and this warning can occur at the very beginning of the drowsiness cycle. Further, the device could be employed as a medical device to detect the state of consciousness or awareness of a patient or accident victim.

The decrease of eyelid movement activity with drowsiness is a common phenomenon that occurs among almost all individuals and therefore the system could be used by almost all persons. Eyelid movement activity can be detected electrically by positioning an electrode just above the eyebrow of an individual in the vicinity of the orbicularus occili muscle. Eyelid movement or blinking by contraction of this muscle produces a small electrical signal which is sensed by the electrode. By positioning a similar reference electrode in the forehead region away from the eyebrow, an electrical reference signal level can be obtained which is useful in discriminating against false signals, such as noise.

Both the reference sensor electrode and the eyebrow sensor electrode will pick up spurious and unwanted background noise, and by using output of the reference electrode sensor as a reference level for the eyebrow electrode, eyebrow movement activity is detected when a voltage is present at the eyebrow electrode that is not present at the reference electrode. By employing high input impedance and high gain amplifiers, a strong eyelid movement detection signal with minimal noise components can be obtained.

A comparator compares the eyelid movement detection signal to a threshold level signal and produces a control signal when the detection signal is significantly characteristically different from the threshold level signal. The comparator serves to discriminate against weak signals indicative of insignificant eyelid movement activity. The control signal resets a timing device whenever significant eyelid movement activity occurs. If the timer is not reset within a selected time interval, e.g., fifteen seconds, it produces a warning signal to activate a warning device which warns the operator that he is starting to become drowsy.

This warning system can be employed by most all individuals as a reliable indicator of drowsiness, is light, compact, requires a minimum of maintenance and adjustment, and provides significant noise rejection characteristics. Because the individual is warned at an early stage of his drowsiness, he is alerted before possible accident or disaster occurs.

Numerous other advantages and features of the present invention will become readily apparent from the following detailed description of the invention and two embodiments thereof, from the claims and from the accompanying drawings.

DETAILED DESCRIPTION OF THE PREFERRED EMBODIMENTS

Figure 1:
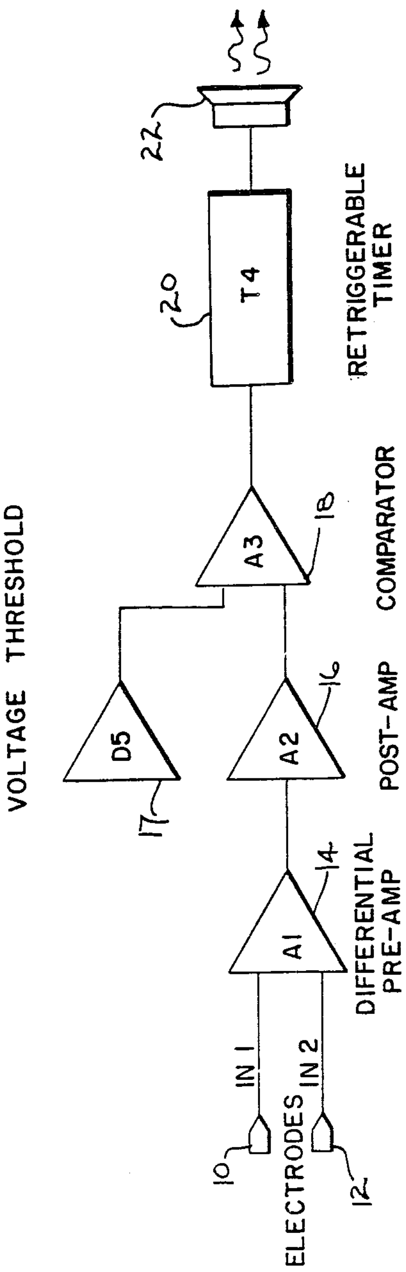
FIG. 1 is a block diagram of the eyelid movement detector main circuit components of the invention.

While this invention is susceptible of embodiment in many forms, there is shown in the drawings and will herein be described in detail two specific embodiments, with the understanding that the present disclosure is to be considered as an exemplification of the principles of the present invention. It is not intended to limit the invention to the embodiments illustrated.

Referring now to the drawing, FIG. 1 shows a block diagram of the drowsiness warning detector incorporating the present invention. Shown on the left are two electrodes, (IN1, IN2), 10, 12, each of which is placed over one eyebrow of an individual. The impedance of the skin layer is about 10 megaohms and the electrodes produce a voltage of about 100 microvolts when significant eyelid movement activity occurs. A different preamp 14 (A1) amplifies this signal and provides a detection signal.

A post amplifier 16 (A2) further amplifies this detection signal and produces an output signal of about 0.1 volts when significant eyelid movement activity occurs. If the post amplifier output signal exceeds a threshold signal level of about 0.1 volts produced by reference circuit 17 (D5), a comparator 18 (A3) produces a control signal. This control signal resets a retriggerable timer 20 (T4). If the retriggerable timer is not reset within a selected time period, e.g., 15 seconds, a switching signal is produced. In normal operation, control signals will be generated at least as often as every 15 seconds, the retriggerable timer 20 (T4) will be reset, and a switching signal will not be produced by the timer. If eyelid activity does not occur for a 15 second period, a switching signal will be produced and will trigger a warning device 22 to produce a signal to warn the operator that he is starting to become drowsy. The warning signal can be an audible sound wave either fixed or varying in frequency or amplitude, or can be a visible light which can also be fixed or varying.

Figure 2:
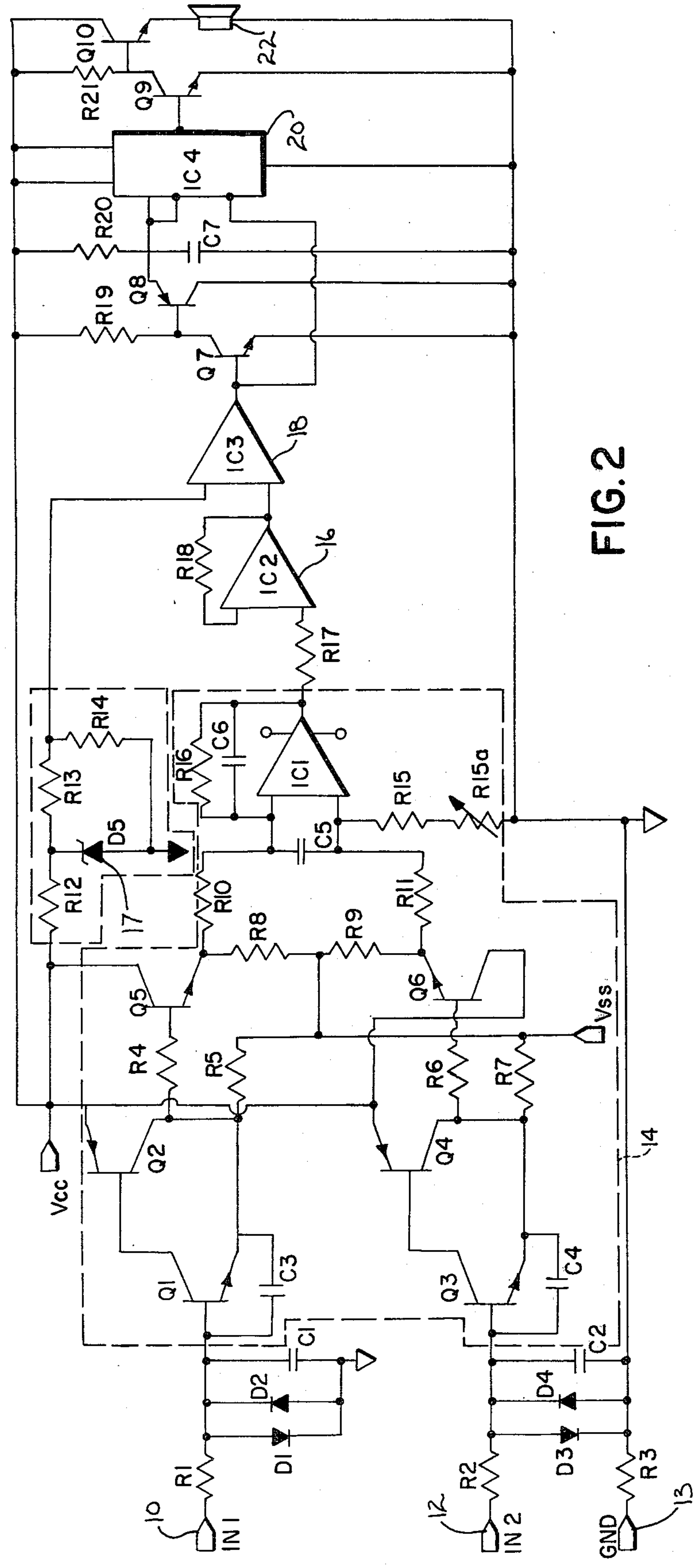
FIG. 2 is an electrical schematic showing a first embodiment of the eyelid movement detector.

FIG. 2 shows the electrical components represented in the block diagram of FIG. 1. At the left are three electrodes 10, 12, 13 which comprise the signal means. IN1 electrode 10 is positioned over the eyebrow of one eye, IN2 electrode 12 is positioned over the eyebrow of the other eye, and the ground reference electrode GND 13 is positioned between IN1 and IN2 and serves as a reference or ground. External noise or vibration will thus excite all three electrodes and no voltage will then be present between IN1 or IN2 and the ground reference electrode GND. However, when eyelid movement activity occurs, a voltage is detected between IN1 or IN2 and the GND electrode and is fed into the differential preamp 14. R1, R2 and R3 are current limiting resistors which protect the circuitry from strong extrinsic signals and maintain a high input impedance for the preamp. Diodes D1, D2, D3 and D4 clip or pinch the input voltage at plus or minus 0.5 volts maximum and protect the circuit from large transient signals. Capacitors C1 and C2 shunt high frequency signals and filter out all signals above 10 kilohertz. Transistors Q1, Q2, Q3 and Q4 comprise two independent Darlington pair amplifiers which amplify the detected voltage. The combination of a PNP and an NPN transistor in each Darlington amplifier minimizes the offset and adds stability to each of the amplifiers. Additionaly, capacitors C3 and C4 add stability to the Darlington amplifiers. The Darlington amplifiers exhibit high input impedance and high current gain. The input current is on the order of 1 picoamp ($10^{-12}$ amp) and the output of the Darlington amplifiers is on the order of 1 nanoamp ($10^{-9}$ amp) when significant eyelid movement activity occurs (i.e., when the electrode voltage is equal to or greater than 100 microvolts). Transistors Q5 and Q6 act as amplifiers which offer high input impedance and current gain. The output voltage of these amplifiers is on the order of 1 millivolt.

The input current required by IC1 is on the order of 300 nanoamps per side. R8, R9, R10, R11 and R16 are chosen to give a voltage gain on the order of 25 and an output voltage of about 25 millivolts. The combination of resistor R16 and capacitor C6 provide a low pass filter and limited band width of about 10–15 kilohertz. IC1 is preferably a 709 integrated circuit. Calibration of A1 is obtained by adjusting variable resistor R15*a*.

The output of IC1 is fed through resistor R17 into IC2, which preferably is an LM741 operational amplifier. Resistors R17 and R18 are chosen so that an input voltage of about 25 millivolts is amplified to just greater than 0.1 volts.

The output of IC2, the detection signal, is fed into a voltage comparator IC3, which is preferably an LM311. This detection signal is compared to a fixed threshold voltage level of 0.1 volts which is generated by a circuit comprised of supply voltage VCC, current limiting resistor R12, a voltage reference source D5 providing a reference level of 4.7 volts, and voltage divider comprised of resistor R13 and R14. When the detection voltage exceeds the threshold level of 0.1 volts, which occurs when the IN1 or IN2 electrode picks up a voltage of 100 microvolts or more relative to the GND electrode, IC3 outputs a control signal which resets the retriggerable timer, indicating that sufficient eyelid movement activity is occuring indicating that the individual is not drowsy.

The output control voltage of IC3 is fed into two inverter transistors Q7 and Q8. R19 is a current limiting resistor connected to the collector of transistor Q7 and the base of transistor Q8. The inverting transistors Q7 and Q8 invert the control signal and feed it into the inverting input of IC4. A non-inverted version of the control signal is preferably fed into the non-inverting input of IC4. IC4 is a monostable multivibrator 555. The output of the IC4 has a low stable state. Selection of resistor R20 and capacitor C7 preferably give the monostable multivibrator a time period of about 15 seconds. This is, of course, adjustable by choosing different R and C values for R20 and C7. If a retrigger pulse is not received by the IC4 by the end of this 15 second time period the monostable multivibrator assumes its low stable state and provides a warning signal to the warning device to warn the individual that he has become drowsy. Therefore, the IC4 must be retriggered by a control signal at least every 15 seconds in order to prevent this monostable multivibrator from reverting to its stable state.

If the monostable multivibrator is not retriggered and the output of IC4 assumes its low stable state, transistor Q9 inverts this low signal to provide a high voltage level to the base of transistor Q10. Transistor Q10 acts as a switch which turns on the speaker, in response to IC4 reverting to its stable state, and allows a voltage potential equal to VCC across the terminals of the speaker. The operator is then warned as to his state of drowsiness and is aroused by the sound of the audible speaker. Any other suitable warning device can be used, such as a light or vibration warning device.

Figure 3:
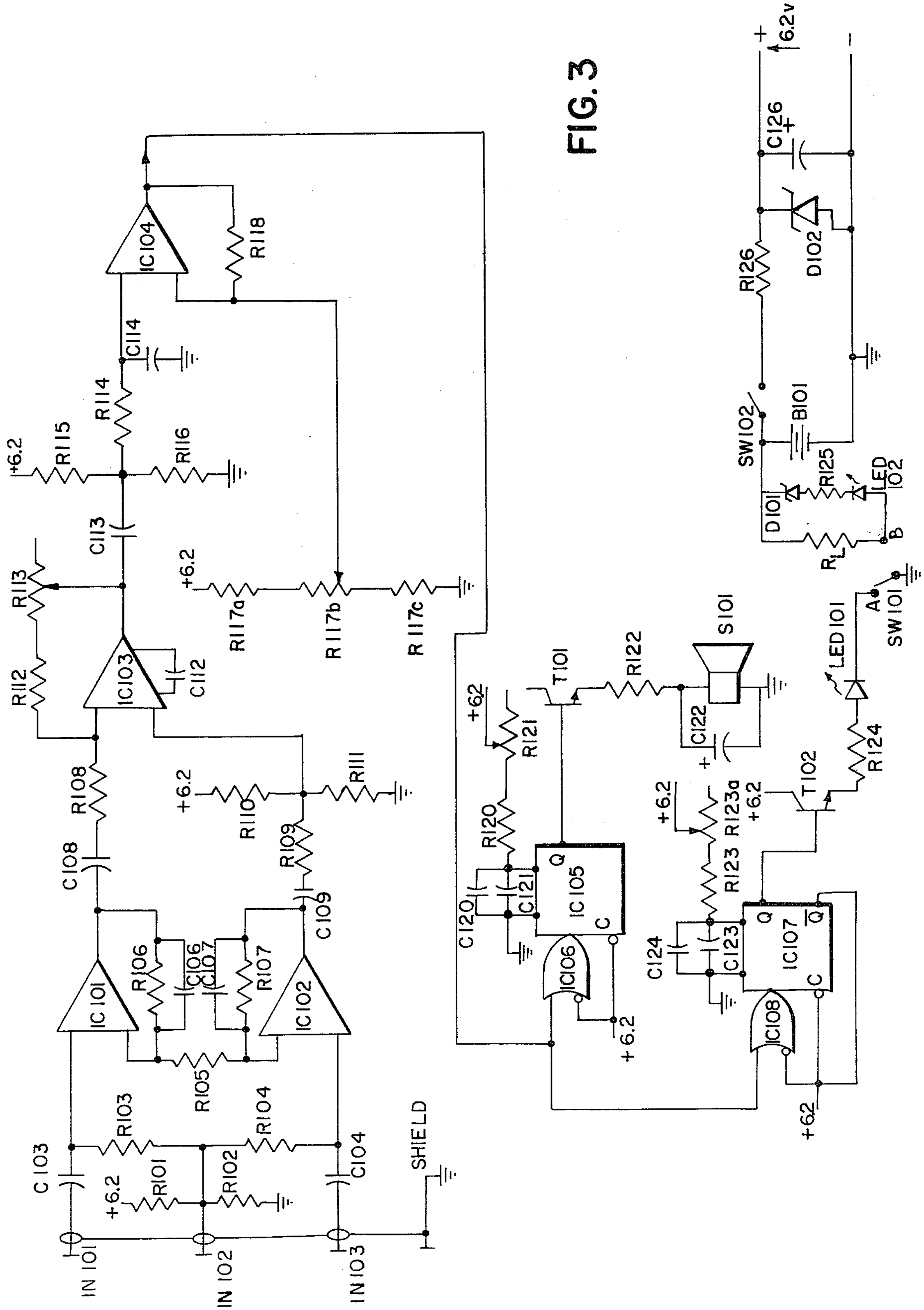
FIG. 3 is an electrical schematic showing a second and more preferred embodiment of the eyelid movement detector.

Referring now to FIG. 3, another preferred embodiment of the instant invention will be described. This embodiment employs the use of MOS components. The illustrated arrangement of embodiment 3 has a favorable common mode rejection while also offering a relatively high input impedance. The high point impedance is necessary because microvolts must be sensed in the presence of many volts of noise. This arrangement also has a large dynamic range. Generally however, this circuit operates similarly to the embodiment illustrated in FIG. 2 as will become more apparent from the following discussion.

Shown at the left-hand side of FIG. 3 are the three input electrodes IN101, IN102 and IN103. As can be seen, 6.2 volts is applied across resistors R101 and R102. Since the resistor values are both 110K ohms, the reference electrode IN102 is at 3.1 volts. Capacitor C103 and resistor R103 provide a long time constant, as do capacitor C104 and resistor R104. C103 and C104 each have a value of 0.047 uf and are matched to within 1% of each other. R103 and R104 each have a value of 10 M ohms.

Amplifiers IC101 and IC102 are operated in common mode rejection relationship. IC101 and IC102 are each a model CA3160E BiMOS op amp. Resistor R105 has a value of 1K ohm with a tolerance of 1%. Resistor R106 and capacitor C106 provide attenuation against high frequency and operate thus as a band pass filter to filter out any signals which may be present especially if the device is used in automobile applications. Resistors R106 and R107 each have a value of 110K ohms with a tolerance of 2% and capacitors C106 and C107 each have a value of 330 pf. Capacitor C108 and resistor R108 provide a shorter time constant relative to the time constant provided by C103 and R103. The same is true of C109 and R109 wherein the two capacitors each have a value of 0.68 uf and the resistors each have a value of 10K ohms with a tolerance of 1%. Resistors R110 and R111 comprise a voltage divider and each have a value of 200K ohms, also with a tolerance of 1%.

Amplifier IC103 is also a model CA3160E op amp. Capacitor C112 connected between appropriate pins thereof, has a value of 330 pf. Resistor R112 connected in feedback fashion, has a value of 100K ohms. Alternatively, a variable resistor R113 could be connected in series with resistor R112 to make adjustments, but with the low tolerances, matched components, this is not necessary.

The configuration of IC102 and IC103 along with the attendant capacitors and resistors comprise an amplifier having ideal performance specifications. The amplifier's first stage of IC101 and IC102 provides all the gain while the second stage, IC103, provides common mode rejection and double-ended to signal-ended conversion. The resistor R105, in relation to resistors R106 and R107 determines the gain of the amplifier, which in this case is about 110.

Moving along to the right of the upper half of FIG. 3, there is shown a voltage divider comprised of resistors R115 and R116 each having a value of 2 M ohms. Capacitors C113 and C114 along with resistor R114 provide attenuation for high radio frequencies. Capacitor C113 has a value of 0.1 uf and capacitor C114 has a value of 100 pf. Resistor R114 has a value of 1 M ohms.

Amplifier IC104 acts as a voltage comparator comparing the voltages at its inputs. The voltage existing at one input is a threshold reference voltage signal obtained by use of a variable resistor serving as a voltage divider. The voltage divider is shown comprising three resistors; resistor R117*a*, variable resistor R117*b*, and resistor R117*c*. *Resistors R117a* and R117*c* each have a value of 180K ohms and resistors R117*b* has a value of 100K ohms. The total voltage drop of this voltage divider is 6.2 volts. Resistors R117*a* and R117*c* may not be necessary and might be eliminated or shorted out. A feedback resistor R118 is connected between the output and the reference input of IC104 and has a value of 4.7 M ohms.

A signal will thus be produced at the output of IC104, when the voltage from IC103 is greater than the threshold voltage. This indicates significant eyelid movement activity to indicate a state of awareness. The output of IC104 is fed into monostable multivibrator IC105 via an inverter-OR gate IC106. The time constant of the multivibrator IC105 is determined by the values of capacitors C120 and C121 and resistors R120 and R121. As illustrated, C120 has a value of 47 uf, C121 has a value of 68uf, R120 has a value of 620K ohms and R21 is a variable resistor having a value of 500K ohms. R121 thus provides a means to adjust the time delay within which a pulse is to be received by the monostable multivibrator IC105 before the alarm mode is entered.

The alarm mode occurs when the monostable multivibrator IC105 goes to its stable state wherein its Q output goes high. This turns on transistor T101 supplying current through resistor R122 to speaker S101. Capacitor C122 has a value of 22uf, R122 has a value of 30 ohms and T101 is identified by part number MPS6514. Transistor S101 should be rated at about 6 volts. Thus, this part of the circuit is substantially similar to the embodiment of FIG. 2.

In this embodiment, another monostable multivibrator, IC107, is present which also receives pulses through its input inverter OR gate IC108. This monostable multivibrator provides a way to give a visual signal indicating when pulses are being received by the monostable multivibrators from the output of the amplifier IC104. The components C123, C124, R123 and R123*a* associated with IC107 have values similar to those associated with IC105. LED101 conducts and gives a visual signal if switch SW101, a momentary single pole double throw SPST is in the normal A position.

Depressing switch SW101, so that point B is connected to ground, provides a way to get a visual indication of the battery condition by putting a known load on the battery through an LED 102 resistor R125 and Zener diode D101. Battery B101 can be a conventional 9 volt battery and provides the overall voltage source for the overall system. Closure of an on-off switch SW102 puts the whole system into the operational mode. A voltage regulator is provided, comprised of resistor R126 having a value of 560 ohms, a Zener diode D102, part IN5234 rated at 6.2 volts/500 mA and a capacitor C126, in parallel with the Zenor diode, having a value of 10 uf. The supply voltage of 6.2 volts is available across the capacitor C126 and Zener diode D102.

As can be seen, the second embodiment is similar in operation and function to the first embodiment of FIG. 2, but is superior in that its components provide for a higher input impedance and better common mode rejection performance due to the MOS components used.

Figure 4:
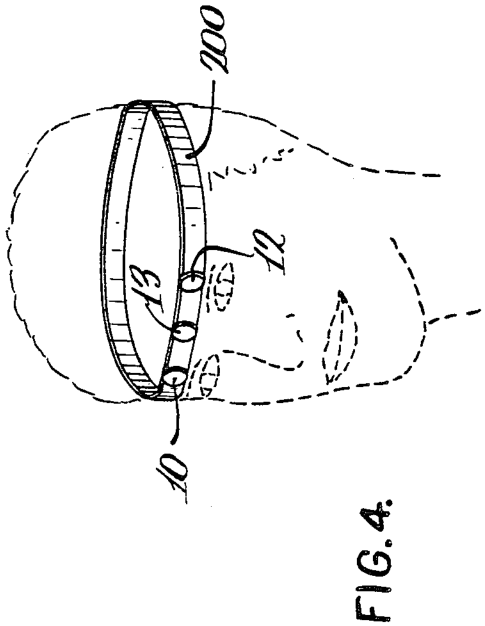
FIG. 4 shows the sensor electrodes mounted on a headband.

The two sensing electrodes 10, 12 and the reference electrode 13 can be easily mounted in a headstrap 200 which can be easily attached and removed by most individuals (see FIG. 4). This headstrap can be easily worn by operators of automobiles, aircraft and/or heavy or dangerous machinery.

The values of the various components identified herein are provided to illustrate satisfactory operational circuits.

From the foregoing, it will be observed that numerous variations and modifications may be effected without departing from the true spirit and scope of the novel concept of the invention. It is to be understood that no limitation with respect to the specific embodiments illustrated herein is intended or should be inferred. It is, of course, intended to cover by the appended claims all such modifications as fall within the scope of the claims.

What is claimed is:

1. An eyelid movement detector and warning device which detects movement of an individual's eyelid comprising:

means for sensing eyelid movement and for providing a detection signal in response to the occurrence of eyelid movement;

means for comparing said detection signal to a threshold signal and for producing a control signal in response to a characteristic of said detection signal being different from a corresponding characteristic of said threshold signal; and timing means responsive to said control signal for producing a switching signal to trigger a warning device in response to the absence of said control signal for a predetermined time period.

2. The eyelid movement detector and warning device of claim 1 wherein said sensing means is comprised of at least two sensors, one being a reference sensor and the other being an eyelid movement sensor, and whereby the detection signal is the difference between a signal characteristic of the eyelid sensor signal and a signal characteristic of the reference sensor signal.

3. The eyelid movement detector and warning device of claim 2 including a second eyelid movement sensor.

4. The eyelid movement detector and warning device of claim 1 including pre-amplification means for amplifying the detection signal.

5. The eyelid movement detector and warning device of claim 1 wherein the signal characteristic is voltage amplitude.

6. An eyelid movement detector and warning device which detects movement of an individual's eyelid comprising:

a reference sensor and an eyelid movement sensor which produces an eyelid movement signal in response to occurrence of eyelid movement;

signal means for producing a detection signal in response to the eyelid movement signal;

means for producing a control signal in response to a characteristic of a detection signal having a preselected characteristic value;

a timer connected to receive control signals, for producing a switching signal in response to the absence of said control signal for a predetermined interval of time; and warning means, responsive to said switching signal, for producing a warning signal.

7. The eyelid movement detector and warning device of claim 6 wherein the reference sensor and the eyelid movement sensor are electrodes in contact with the skin which produce current in response to muscle movement.

8. The eyelid movement detector and warning device of claim 6 wherein the eyelid movement sensor is positioned generally above the center of one eyebrow of an individual and wherein the reference sensor is positioned generally in the middle of the individual's forehead.

9. The eyelid movement detector and warning device of claim 6 wherein the signal means produces a detection voltage signal in response to the voltage amplitude signal characteristic from the eyelid movement sensor exceeding a reference voltage amplitude signal characteristic.

10. The eyelid movement detector and warning device of claim 6 wherein the control signal production means produces a voltage control signal in response to a characteristic amplitude of the detection signal being greater than the characteristic amplitude of a reference signal.

11. The eyelid movement detector and warning device of claim 10 wherein the control signal production means is a voltage comparator and wherein the characteristic amplitudes compared are voltage amplitudes.

12. The eyelid movement detector and warning device of claim 6 wherein the timer is a monostable multivibrator having a low voltage stable state.

13. The eyelid movement detector and warning device of claim 6 wherein the predetermined interval of time is about 15 seconds.

14. The eyelid movement detector and warning device of claim 6 wherein the warning means is a transducer which produces sound in response to said switching signal.

15. An eyelid movement detector and warning device which detects movement of an individual's eyelids comprising:

a reference sensor electrode located generally in the middle of an individual's forehead;

two eyelid movement sensor electrodes each of which are located generally above the middle of an individual's eyebrow and which produce an eye movement voltage signal with respect to said reference electrode in response to movement of the respective eyelid;

a differential amplifier for amplifying the difference between the amplitudes of said eye movement voltages and the voltage amplitude of said reference sensor electrode and for producing an output voltage signal;

a voltage comparator which produces a voltage control signal in response to the voltage amplitude characteristic differential pre-amp output voltage signal being greater than the voltage amplitude characteristic of a predetermined threshold reference voltage signal;

a monostable multivibrator responsive to said voltage control signals and triggered to its unstable state in response thereto;

a timer within said monostable multivibrator which returns the multivibrator to its stable state in response to the absence of a voltage control signal for a predetermined time interval;

and warning means connected to said monostable multivibrator and responsive to an output from said monostable multivibrator in its stable state for producing an audible signal.

16. The eyelid movement detector and warning device of claim 15 wherein the predetermined time interval is about 15 seconds.

17. The eyelid movement detector and warning device of claim 15 wherein the reference sensor electrode and the two eyelid movement sensor electrodes are mounted on a headband.

18. The eyelid movement detector and warning device of claim 15 wherein said differential amplifier and voltage comparator are MOS components.

* * * * *